(12) United States Patent
Song et al.

(10) Patent No.: US 9,411,416 B2
(45) Date of Patent: Aug. 9, 2016

(54) COMPUTER DEVICE OPERABLE WITH USER'S EYE MOVEMENT AND METHOD FOR OPERATING THE COMPUTER DEVICE

(76) Inventors: Wenjuan Song, Beijing (CN); Jianping Song, Beijing (CN); Lin Du, Beijing (CN)

( * ) Notice: Subject to any disclaimer, the term of this patent is extended or adjusted under 35 U.S.C. 154(b) by 67 days.

(21) Appl. No.: 14/128,625

(22) PCT Filed: Jun. 24, 2011

(86) PCT No.: PCT/CN2011/076288
§ 371 (c)(1),
(2), (4) Date: Dec. 22, 2013

(87) PCT Pub. No.: WO2012/174743
PCT Pub. Date: Dec. 27, 2012

(65) Prior Publication Data
US 2014/0125585 A1    May 8, 2014

(51) Int. Cl.
*G06F 3/01* (2006.01)
*H04N 13/04* (2006.01)
(Continued)

(52) U.S. Cl.
CPC ............... *G06F 3/013* (2013.01); *G06F 3/017* (2013.01); *A61B 3/113* (2013.01); *A61B 2017/00216* (2013.01); *H04N 13/0484* (2013.01)

(58) Field of Classification Search
CPC .......... G06F 3/013; G06F 3/01; G06F 3/017; G06F 3/04842; G06F 3/012; G06F 3/041; G06F 3/011; G06F 3/0484; G06F 3/0346; G06F 3/0486; G06F 3/04883; G06F 3/005; G06F 3/038; G06F 17/30867; B60W 50/10; G09G 2354/00; H04N 13/0484; G02B 27/017; G02B 27/0179; G02B 27/021; G02B 27/01; G02B 27/02; G02B 2027/014; G02B 2027/0138; G02B 2027/0187; G02B 2027/0181; A61B 2017/00216; G06T 19/006; G06T 11/60; G06T 7/208; G06K 9/00604; G06K 9/00335

See application file for complete search history.

(56) References Cited

U.S. PATENT DOCUMENTS 4,973,149 A * 11/1990 Hutchinson .................. 351/210
5,360,971 A * 11/1994 Kaufman ............... A61B 3/113
                                                       250/221

(Continued)

FOREIGN PATENT DOCUMENTS

CN          1694045       11/2005
CN        101291364       10/2008

(Continued)

OTHER PUBLICATIONS

Kumar et al., "Gaze-Enhanced Scrolling Techniques", UIST'07, Oct. 7-10, 2007, ACM Symposium.

(Continued)

*Primary Examiner* — Ariel Balaoing
*Assistant Examiner* — Darlene M Ritchie
(74) *Attorney, Agent, or Firm* — Meagher Emanuel Laks Goldberg & Liao, LLP

(57) ABSTRACT

The present invention relates to a method for operating a computer device with user's eye movement. The method comprises the steps of detecting the user's eye movement, analyzing the user's eye movement to specify an eye movement pattern in the detected user's eye movement and a time period for completing the eye movement pattern, determining a command associated with a combination of the eye movement pattern and the time period and operating the device according to the command.

8 Claims, 8 Drawing Sheets

(51) Int. Cl.
*A61B 3/113* (2006.01)
*A61B 17/00* (2006.01)

(56) References Cited

U.S. PATENT DOCUMENTS

| | | | | |
|---|---|---|---|---|
| 5,517,021 | A * | 5/1996 | Kaufman | A61B 3/113 250/221 |
| 5,751,260 | A * | 5/1998 | Nappi | G06F 3/013 340/4.13 |
| 5,835,083 | A * | 11/1998 | Nielsen | G06F 1/3209 345/211 |
| 6,106,119 | A * | 8/2000 | Edwards | 351/209 |
| 6,195,640 | B1 | 2/2001 | Mullaly et al. | |
| 6,873,314 | B1 * | 3/2005 | Campbell | A61B 3/113 345/156 |
| 7,091,471 | B2 | 8/2006 | Wenstrand et al. | |
| 8,331,993 | B2 * | 12/2012 | Lee | H04M 1/67 340/571 |
| 8,451,246 | B1 * | 5/2013 | Scholler | G06F 3/04883 345/173 |
| 8,655,796 | B2 * | 2/2014 | Udani | G06F 19/363 705/2 |
| 2003/0098885 | A1 * | 5/2003 | Yabe | G06F 3/0485 715/785 |
| 2005/0199783 | A1 * | 9/2005 | Wenstrand et al. | 250/214.1 |
| 2006/0281969 | A1 | 12/2006 | Wang et al. | |
| 2007/0024579 | A1 * | 2/2007 | Rosenberg | G06F 3/013 345/156 |
| 2007/0226646 | A1 * | 9/2007 | Nagiyama | G06F 3/016 715/784 |
| 2008/0143674 | A1 | 6/2008 | Molander et al. | |
| 2008/0211766 | A1 | 9/2008 | Westerman et al. | |
| 2009/0077501 | A1 * | 3/2009 | Partridge | G06F 3/017 715/846 |
| 2009/0289895 | A1 | 11/2009 | Nakada et al. | |
| 2009/0315827 | A1 * | 12/2009 | Elvesj et al. | 345/157 |
| 2010/0182232 | A1 | 7/2010 | Zamoyski | |
| 2010/0191727 | A1 * | 7/2010 | Malik | G06F 17/30867 707/734 |
| 2011/0077548 | A1 * | 3/2011 | Torch | A61B 3/112 600/558 |
| 2011/0270123 | A1 * | 11/2011 | Reiner | 600/558 |
| 2012/0105486 | A1 * | 5/2012 | Lankford | G06F 3/013 345/661 |
| 2013/0106921 | A1 | 5/2013 | Nakayama | |

FOREIGN PATENT DOCUMENTS

| | | |
|---|---|---|
| CN | 101308400 | 11/2008 |
| CN | 101441513 | 5/2009 |
| CN | 101681201 | 3/2010 |
| JP | H06318235 | 11/1994 |
| JP | 2000010722 | 1/2000 |
| JP | 2000020534 | 1/2000 |
| JP | 2006107048 | 4/2006 |
| JP | 2007310815 | 11/2007 |
| JP | 2009075937 | 4/2009 |
| JP | 2010102581 | 5/2010 |
| JP | 2012063899 | 3/2012 |
| KR | 2009127779 | 12/2009 |
| WO | WO2006100645 | 9/2006 |

OTHER PUBLICATIONS

Porta et al., "WyeB, and Eye-Controlled Web Browser for Hands-Free Navigation", IEEE, 2009, Catania, Italy, May 21-23, 2009.
Search Report dated Mar. 29, 2012.
Wong et al., "Eye Tracker for Mobile Device", Research Disclosure 535068, Nov. 10, 2008, pp. 1-2.
Milekic, S., "The more you look the more you get: intention-based interface using gaze tracking", Museums and the web 2003: Proceedings, Jan. 1, 2003, pp. 1-17.

* cited by examiner

COMPUTER DEVICE OPERABLE WITH USER'S EYE MOVEMENT AND METHOD FOR OPERATING THE COMPUTER DEVICE

This application claims the benefit, under 35 U.S.C. §365 of International Application PCT/CN2011/076288, filed Jun. 24, 2011, which was published in accordance with PCT Article 21(2) on Dec. 27, 2012 in English.

FIELD OF THE INVENTION

The present invention relates to a computer device operable with user's eye movement and a method for operating a computer device with user's eye movement.

BACKGROUND OF THE INVENTION

An electronic book (also referred to as e-Book, eBook or digital book) is known as a text and image-based publication in digital form produced on, published by, and readable on computers or other digital devices. eBooks are usually read on dedicated hardware devices known as eReaders or eBook devices. Computer devices such as smart-phones can also be used to read eBooks.

As more people get to use a computer device for reading eBooks, more convenient operations for operating the computer device are expected.

Eye tracking is one of research hotspots. Eye tracking is the process of measuring the point of eye gaze and the motion of a user's eye relative to the head. There are a number of methods for measuring eye movement. The most popular variant uses video images from which the eye position is extracted. Detecting of eye gaze is used in a lot of human computer interaction applications. There are both intrusive and nonintrusive approaches to estimate the eye gaze. For the intrusive techniques, a user needs to wear a headgear camera to fix the position of the eyes with the view of screen on the camera, or use an infrared light on camera to detect the eyes. For the nonintrusive approaches, a user only needs a simple camera for imaging the user's eye and does not have to wear any other equipment. At currently, most of computer devices such as smart-phones and portable electronic game machines are provided with a camera for imaging a user and can be as eReaders.

Movement Pattern Analysis (MPA) is a comprehensive system for assessing an individual's core motivations in decision-making processes, based on the disciplined analysis of nonverbal behavior.

An eye tracking apparatus which recognizes a user's eye movement pattern is shown in U.S. 20080143674A1.

An aim of the present invention is to provide more convenient operations with a user's eye movement for operating a computer device.

SUMMARY OF THE INVENTION

According to an aspect of the present invention, there is provided a computer device operable with a user's eye movement. The computer device comprises means for detecting the user's eye movement, means for analyzing the user's eye movement to specify an eye movement pattern in the detected user's eye movement and a time period for completing the eye movement pattern, means for determining a command associated with a combination of the eye movement pattern and the time period and means for operating the device according to the command.

According to another aspect of the present invention, there is provided a method for operating a computer device with user's eye movement. The method comprises the steps of detecting the user's eye movement, analyzing the user's eye movement to specify an eye movement pattern in the detected user's eye movement and a time period for completing the eye movement pattern, determining a command associated with a combination of the eye movement pattern and the time period and operating the device according to the command.

BRIEF DESCRIPTION OF DRAWINGS

These and other aspects, features and advantages of the present invention will become apparent from the following description in connection with the accompanying drawings in which.

DETAIL DESCRIPTION OF PREFERRED EMBODIMENTS

In the following description, various aspects of an embodiment of the present invention will be described. For the purpose of explanation, specific configurations and details are set forth in order to provide a thorough understanding. However, it will also be apparent to one skilled in the art that the present invention may be practiced without the specific details present herein.

Figure 1:
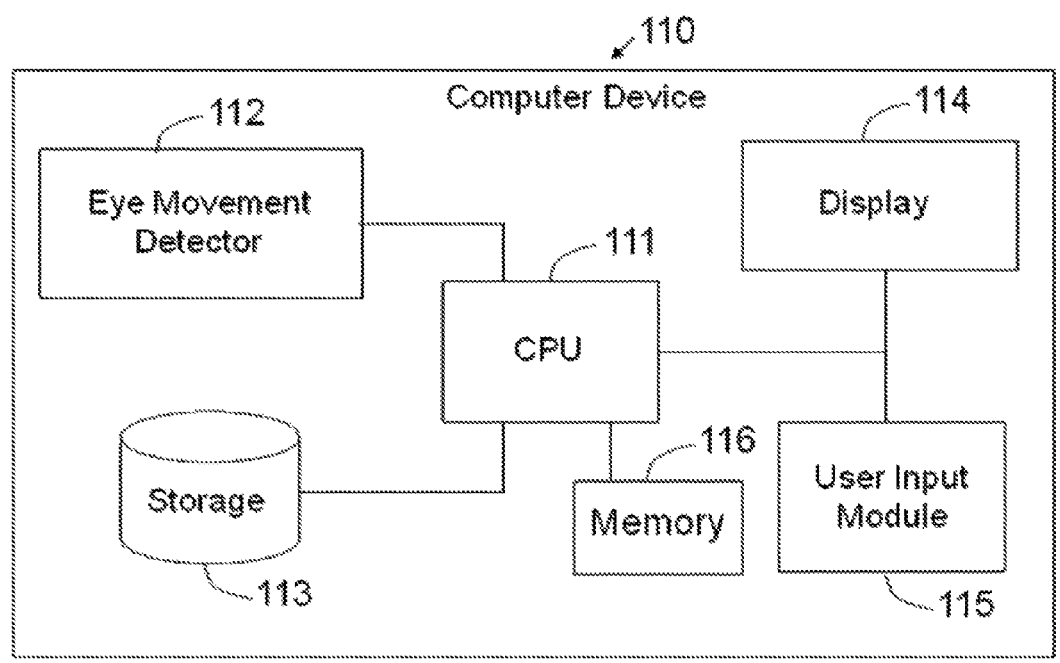
FIG. 1 is an exemplary block diagram of a computer device according to an embodiment of the present invention.

FIG. 1 illustrates an exemplary block diagram of a computer device 110 according to an embodiment of the present invention. The computer device 110 can be a tablet, smart-phone, eBook-reader and so on. The computer device 110 comprises a CPU (Central Processing Unit) 111, an eye movement detector 112, a storage 113, a display 114 and an user input module 115. A memory 116 such as RAM (Random Access Memory) may be connected to the CPU 111 as shown in FIG. 1.

The eye movement detector 112 is an element for detecting an eye of a user of the device 110 and monitoring the motion of the eye and the eye gaze. The eye movement detector 112 is also configured to detect and collect eye gaze positions on the display 114 and to measure a time for each eye gaze. The eye movement detector 112 can employ many different types of techniques for the eye gaze tracking purpose. For example, the eye movement detector 112 can employ three steps to realize the eye gaze tracking: in the first step the eye on the user's face is detected based on the Haar-like features, in the second step tracking the motion of the eye is performed using the Lucas Kanade algorithm and in the third step the eye gaze is detected using Gaussian processes. A person skilled in the art will recognize that the above-described technique is not only a solution for the eye gaze tracking and that many other techniques can be used for the eye gaze tracking.

The display 114 is configured to visually present text, image, video and any other contents to a user of the device 110. The display 114 can be a touch-screen so that it can provide a possibility to the user to operate the device 110 on the display 114 in addition to the user input module 115.

The user input module 115 may include keys or buttons on the device 110 to input characters or commands and also comprise a function to recognize the characters or commands input with the keys or buttons. The user input module 115 can be an option if the display 114 is a touch-screen and the device 110 is configured so that characters or commands can be input on the display 114.

The storage 113 is configured to store software programs and data for the CPU 111 to drive and operate the eye movement detector 112, the display 114 and the user input module 115 as will be explained below.

Figure 2A:
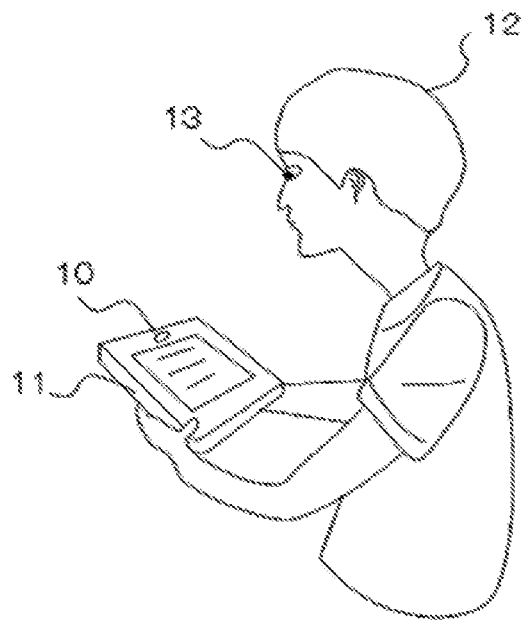
FIG. 2A illustrates a basic environment of the use of the computer device according to an embodiment of the present invention.
Figure 2B:
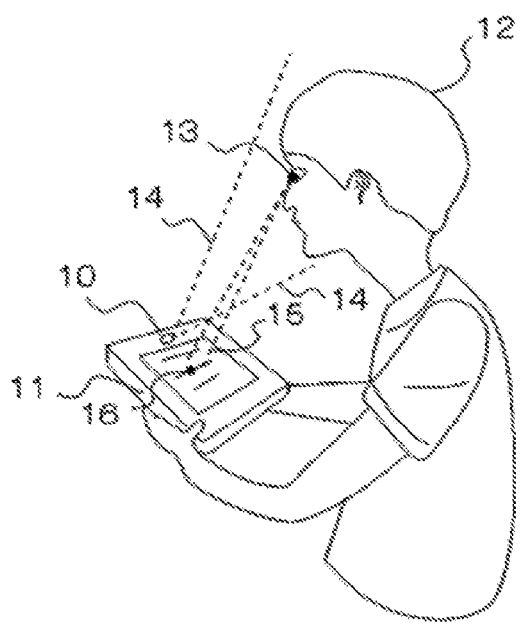
FIG. 2B illustrates the same basic environment as shown in FIG. 2A except for the added optical lines.

FIG. 2A illustrates a basic environment of the use of the computer device according to an embodiment of the present invention. FIG. 2B illustrates the same basic environment as shown in FIG. 2A except for the added optical lines. In FIGS. 2A and 2B, the computer device 110 shown in FIG. 1 is indicated with the reference number "11".

FIGS. 2A and 2B show that user 12 is reading or browsing contents presented on the display of the device 11. The device 11 is equipped with a camera 10 for imaging the face of the user 12 to detect eyes of the user 12 and to monitor the motion of the eyes and the eye gaze. The camera 10 is responsible for capturing the face of the user 12 and for detecting of eye gaze point 16 of the user 12. The camera 10 may be an element of the eye movement detector 112 shown in FIG. 1.

In FIG. 2B, the dashed lines 14 represent a field-of-view or range of the camera 10. The general area of the user's attention is approximately shown by two dashed lines 15.

Figure 3:
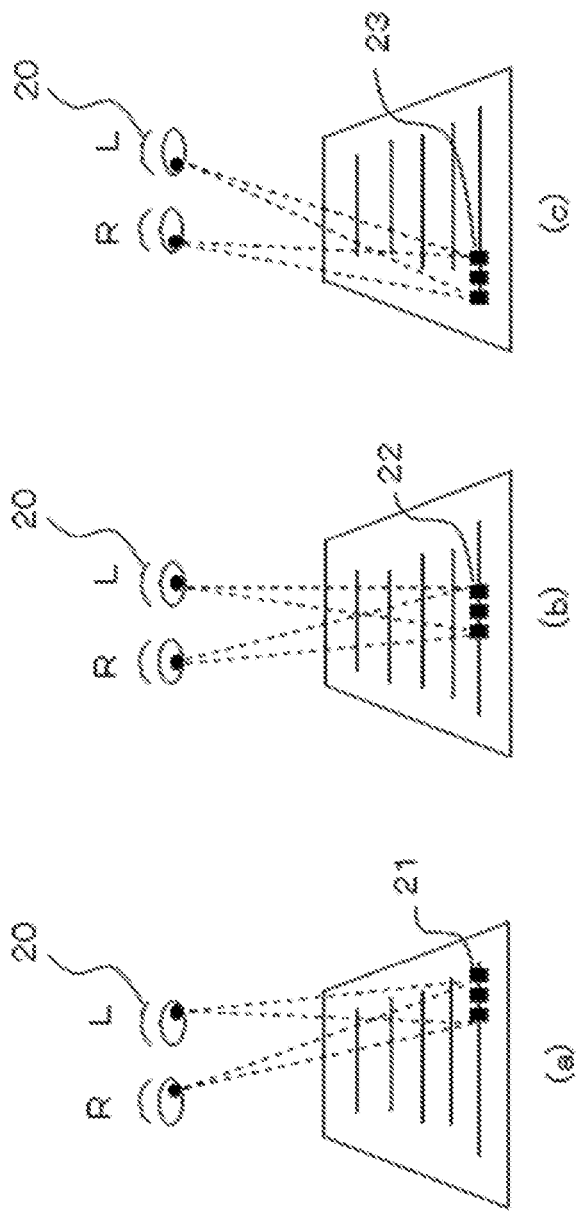
FIGS. 3 (a) to (c) illustrate a basic reading process for reading one text line on a page presented on the display of the computer device from left to right of the text line.

FIGS. 3 (*a*) to (*c*) illustrate a basic reading process for reading one text line on a page presented on the display of the device 11 from left to right of the text line. The left and right eyes 20 of the user move during the reading process. As shown in FIG. 3(*a*), the gaze point 21 is located on the front of the text line at the beginning of the reading process. Then the gaze point 22 moves to the middle of the text line as shown in FIG. 3(*b*) and finally the gaze point 23 moves to the end of the text line as shown in FIG. 3(*c*). These eye movements are detected and time periods for each eye gaze on the text line are measured by the eye movement detector 112 (FIG. 1). The total time for reading the one text line is approximately calculated by summing the time periods for each eye gaze on the text line by the CPU 111 shown in FIG. 1.

Figure 4:
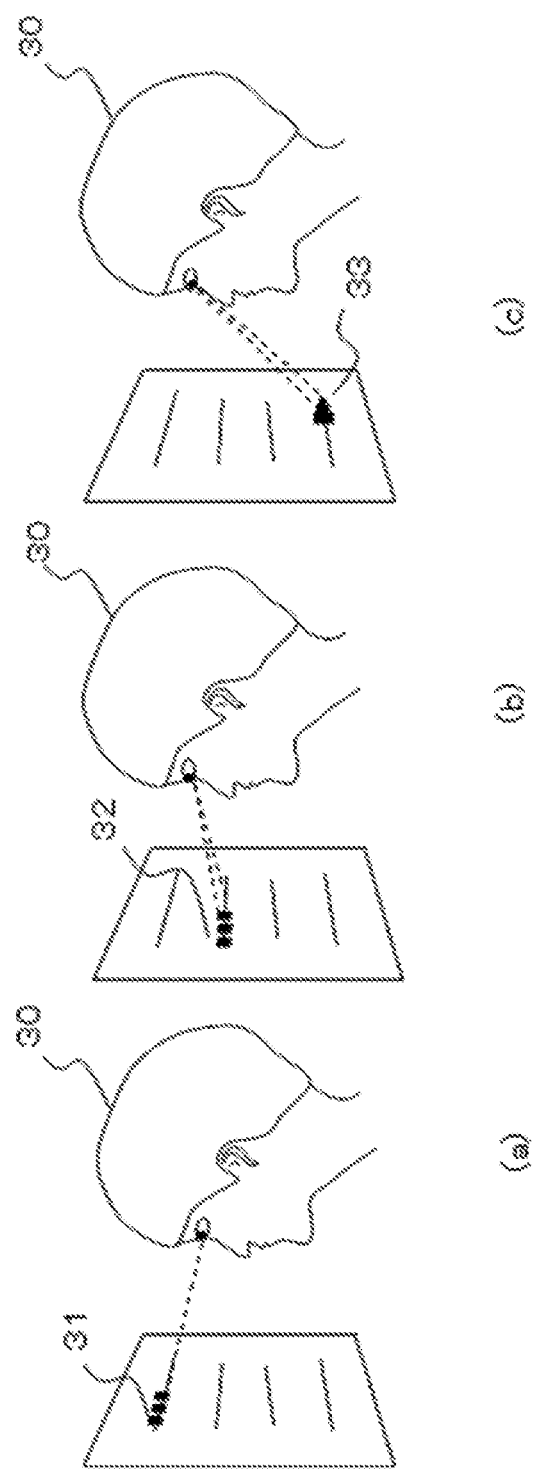
FIGS. 4 (a) to (c) illustrate a basic reading process for reading a page presented on the display of the computer device from the top to the bottom of the page.

FIGS. 4 (*a*) to (*c*) illustrate a basic reading process for reading an entire page presented on the display of the device 11 from the top to the bottom of the page. As shown in FIG. 4(*a*), at first, the user 30 reads the first text line 31 on the page from left to right of the text line 31. Then the user 30 reads the second text line 32 from left to right of the text line 32 and repeats the same reading process for the other text lines (FIG. 4(*b*)). Finally, the user 30 reads the last text line 33 from left to right of the text line 33 (FIG. 4(*c*)). In the same manner as described with reference to FIGS. 3 (*a*) to (*c*), eye movements during the user 30 reads the text lines on the page are detected and time periods for each eye gaze on the text lines are measured by the eye movement detector 112 (FIG. 1). The total time for reading the page is approximately calculated by summing the time periods for each eye gaze on the text lines by the CPU 111 (FIG. 1).

Figure 5:
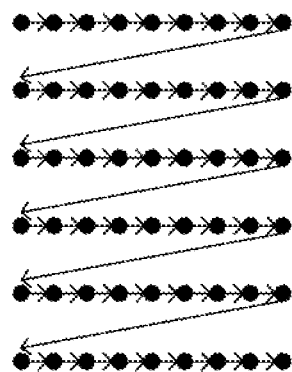
FIG. 5 shows eye movement pattern detected as a result of the reading process for reading a page presented on the display of the computer device shown in FIGS. 4 (a) to (c)

As a result of the reading process for reading a page presented on the display of the device shown in FIGS. 4 (*a*) to (*c*), eye movement pattern as illustrated in FIG. 5 is detected by the device. Each black point shown in FIG. 5 indicates the user's eye gaze point. The arrows mean moving direction of the user's eye gaze point. As can be seen from FIG. 5, the user's eye gaze point moves in zigzag-shape from left to right of each text line and from top text line to bottom text line.

In this basic reading process shown in FIGS. 4 (*a*) to (*c*), for example, the device 11 (FIG. 2A and 2B) is configured to flip a page presented on the display to the next page when the user reads the page on the display from beginning to end.

Figure 6:
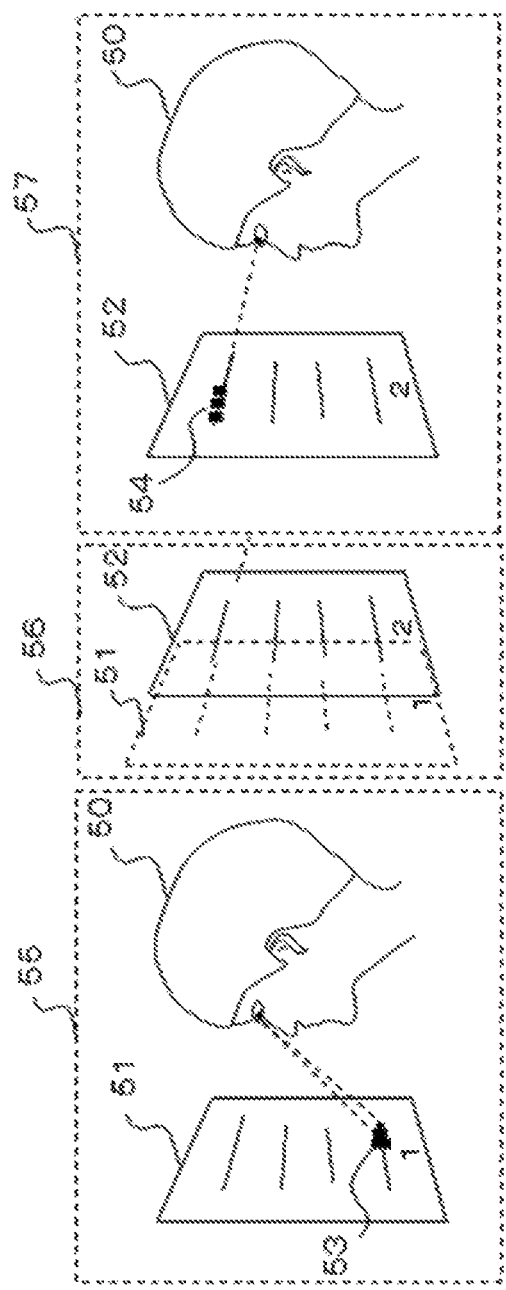
FIG. 6 illustrates on how a page shown on the display of the computer device will be scrolled to the next page according to the eye movement pattern shown in FIG. 5.

The operation mechanism for flipping the page on the display will be explained here with reference to FIGS. 1, 5 and 6. In the storage 113 of the device 110, a table including eye movement patterns and commands is stored. In the table, each command is associated with respective eye movement pattern. When the user 50 reads the page 51 from beginning to end 53 as illustrated in module 55 in FIG. 6, the zigzag-shaped eye movement pattern shown in FIG. 5 is detected using the CPU 111 and the eye movement detector 112. Then the CPU 111 compares the detected eye movement pattern with the eye movement patterns in the table stored in the storage 113. If an eye movement pattern that matches the detected eye movement pattern is found in the table, the CPU 111 executes a command associated with the matched eye movement pattern in the table. If the command is "flip a page on the display", then the page 51 on the display will be scrolled to the next page 52 by the CPU 111 as illustrated in module 56 in FIG. 6. According to an embodiment of the present invention, page 51 presented on the display of the device can be flipped with the user's eye movement detected by the eye movement detector 112 (FIG. 1) which may include the camera 10 (FIGS. 2A and 2B) as described above and then the user 50 can begin to read next page 52 from the beginning 54 as illustrated in module 57 in FIG. 6.

Figure 7:
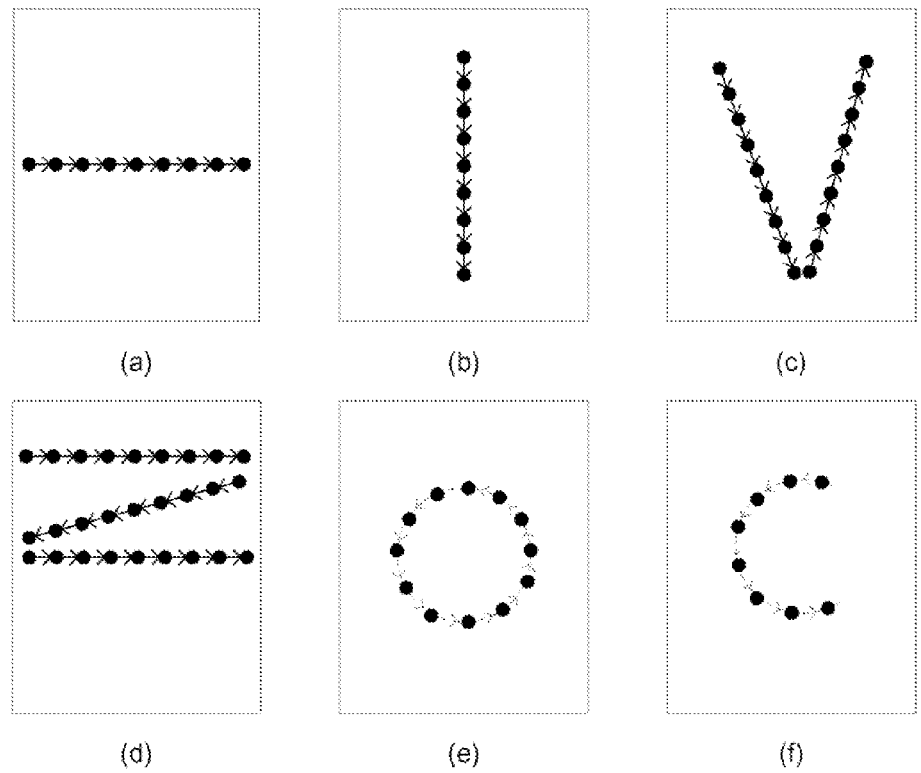
FIGS. 7 (a) to (f) show different kinds of combinations of eye movement pattern and time period for completing the eye movement pattern which combinations generate different kinds of commands for operating the computer device according to the present invention.

FIGS. 7 (*a*) to (*f*) show different kinds of combinations of eye movement pattern and time period for completing the eye movement pattern which combinations generate different kinds of commands for operating the computer device according to the present invention.

FIG. 7 (*a*) illustrates an eye movement pattern in which eye gaze point moves from left to right. A "LEFT" command is associated with the combination of this eye movement pattern and a threshold time period T for completing this eye movement pattern. If this eye movement pattern is detected and the time period t for completing the eye movement pattern is less than the predetermined threshold time period T, the "LEFT" command is executed so that the previous page of the content such as eBook comes from left side and to be shown on the display.

FIG. 7(*b*) shows an eye movement pattern in which eye gaze point moves from top to down. A "NEXT" command is associated with combination of this eye movement pattern and a threshold time period T for completing this eye movement pattern. If this eye movement pattern is detected and the time period t for completing the eye movement pattern is less than the predetermined threshold time period T, the "NEXT" command is executed to show next page of the content on the display.

FIGS. 7 (c) to (f) show further different eye movement patterns. Similar to the cases as shown in FIGS. 7 (a) and (b), commands are associated with combination of an eye movement pattern and a threshold time period T for completing the eye movement pattern and corresponding command is executed if any one of the eye movement patterns shown in FIGS. 7 (c) to (f) are detected and the time period t for completing the eye movement pattern is less than the predetermined threshold time period T. In these examples, the eye movement pattern in FIG. 7 (c) may be associated with a "VERSION" command for indicating the version of the content being presented on the display, the eye movement pattern in FIG. 7 (d) may be associated with an "END" command for jumping to the last page of the content, the eye movement pattern in FIG. 7 (e) may be associated with an "HOME" command for jumping to the first page of the content and the eye movement pattern in FIG. 7 (f) may be associated with an "ROTATE" command for rotating the content being presented on the display. These commands and combinations of eye movement pattern and threshold time period are associated with each other and stored in the storage 113 (FIG. 1).

In the above-described examples, no commands will be executed if the time period t is T or more. It is recognized that the user is just reading or watching the content on the display when the time period t fulfills T ≤ t.

It should be noted that more different threshold time periods can be associated with an eye movement pattern. Referring to FIG. 7 (a) as an example, threshold time period T/2 can be associated with the eye movement pattern in addition to the above-described threshold time period T. In this example, the "LEFT" command may be executed so that two or more previous page comes from left side and shows the page on the display if the time period t for completing the detected eye movement pattern fulfills t<T/2, whereas a single previous page comes from left side to be shown on the display if the time period t fulfills 2/T≤t<T. As can be seen from these examples, a plural of commands can be generated using a single eye movement pattern by associating a plural of threshold time periods with the single eye movement pattern.

Further, it should be noted that different positions of eye movement pattern to be tracked on the display can be associated with the eye movement pattern in addition to the threshold time period(s).

Figure 8:
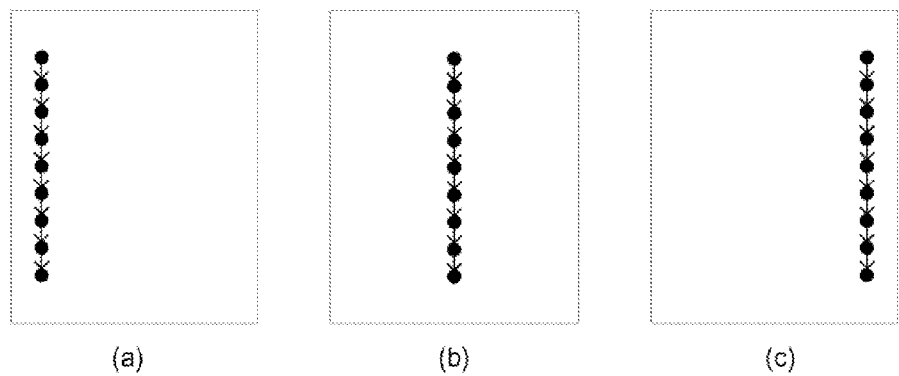
FIGS. 8 (a) to (c) illustrate eye movement patterns tracked at different positions on the display.

FIGS. 8 (a) to (c) illustrate that eye movement patterns are tracked at different positions on the display. It is shown that the eye movement pattern is tracked on left side of the display (FIG. 8(a)), on the middle of the display (FIG. 8(b)) and on right side of the display (FIG. 8(c)).

Provided that threshold time period T is associated with the eye movement pattern in which eye gaze point moves from top to down, for examples, a "Font Size" command can be associated with the combination of the eye movement pattern, threshold time period T for completing this eye movement pattern and the position of the eye movement pattern tracked on the display (left side position as shown in FIG. 8 (a)), a "NEXT" command can be associated with the combination of the eye movement pattern, threshold time period T for completing this eye movement pattern and the position of the eye movement pattern tracked on the display (middle position as shown in FIG. 8 (b)) and a "Zooming" command can be associated with the combination of the eye movement pattern, threshold time period T for completing this eye movement pattern and the position of the eye movement pattern tracked on the display (right side position as shown in FIG. 8 (c)).

In a condition that the eye movement pattern as shown in FIGS. 8 (a) to (c) is detected and the time period t for completing the eye movement pattern is less than the predetermined threshold time period T;
1) if the eye movement pattern is tracked on left side of the display as shown in FIG. 8 (a), the "Font Size" command is executed to allow the user to adjust the font size on the display;
2) if the eye movement pattern is tracked on the middle of the display as shown in FIG. 8 (b), the "NEXT" command is executed to show next page of the content on the display; and
3) if the eye movement pattern is tracked on the right side of the display as shown in FIG. 8 (c), the "Zooming" command is executed to enlarge the content on the display.

Of course, more different threshold time periods can be associated with each of the different positions of the eye movement pattern. More commands can be generated using a single eye movement pattern by associating different threshold time periods and different positions of eye movement pattern on the display with the single eye movement pattern, compared to the case in which either different threshold time periods or different positions of eye movement pattern is associated with the single eye movement pattern.

Different combinations of eye movement pattern and threshold time period are stored in the storage 113 (FIG. 1). Each combination may include position of the eye movement pattern on the display. Also, different commands are stored in the storage 113 in a state that the different commands are associated with the respective combination in the storage 113. These different combinations and their associated commands may be stored in the storage in a table format.

It should be noted that an eye movement patterns formed by a user on the display may not be exactly the same as one of the eye movement patterns indicated in FIGS. 7 and 8 and that, in the above described embodiment of the present invention, an eye movement pattern may be detected even if the eye movement pattern is deformed in a certain tolerant range compared to its reference eye movement pattern.

Also it should be noted that relative size of each eye movement pattern shown in FIGS. 7 and 8 with respect to the size of the display is not limited to the examples illustrated in FIGS. 7 and 8. The eye movement patterns on the display can be any size as long as the eye movement patterns can be detected by the device.

Figure 9:
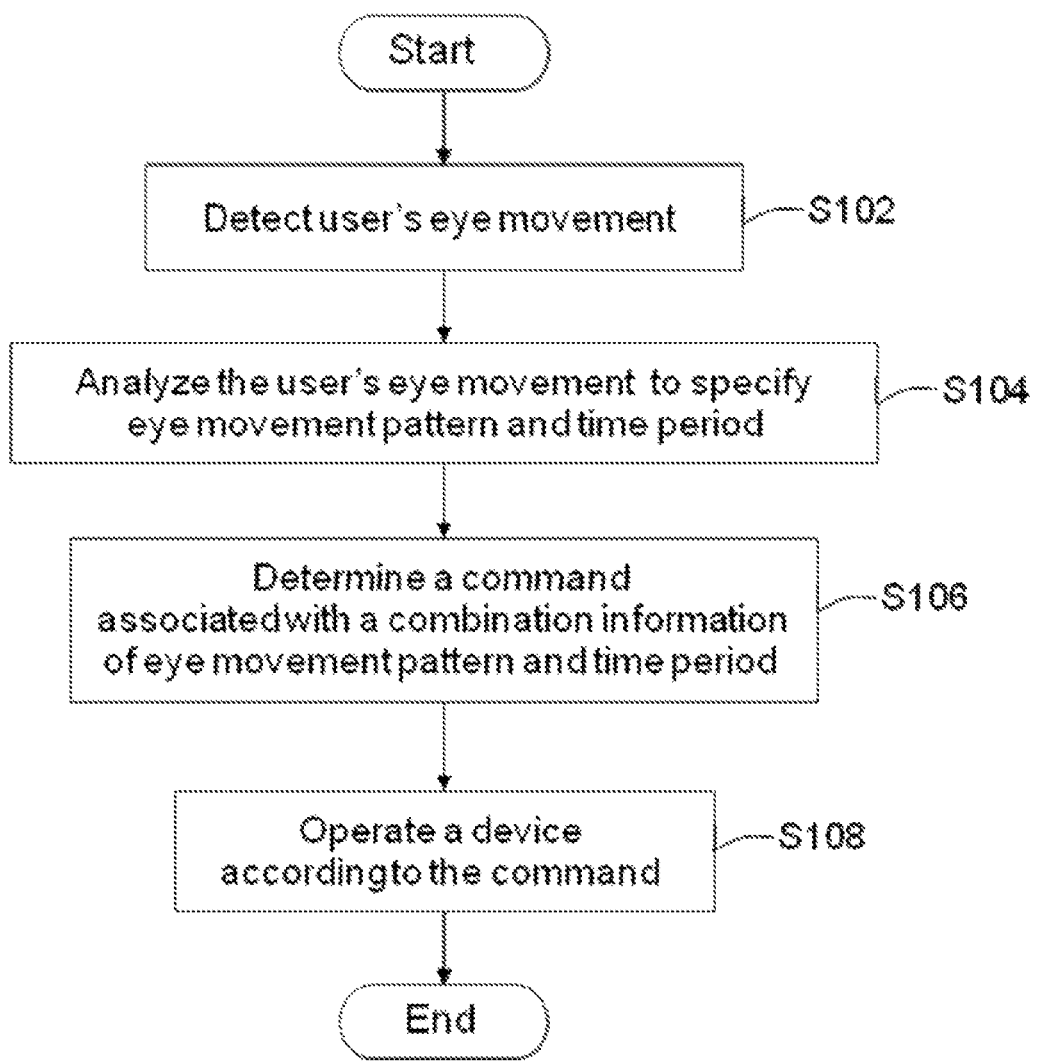
FIG. 9 is a flow chart showing a method for operating the computer device with user's eye movement according to an embodiment of the present invention.

FIG. 9 is a flow chart showing a method for operating the computer device with user's eye movement according to an embodiment of the present invention. The method for operating the computer device will be described below with reference to FIGS. 1 and 9.

At step S102, eye movement of a user of the computer device 110 is detected by means of the eye movement detector 112 of the device 110. In this step, an eye of the user of the device 110 is detected and the motion of the eye and the eye gaze are monitored by the eye movement detector 112. Also each eye gaze position on the display 114 is detected and time for each eye gaze is measured by the eye movement detector 112.

At step S104, the detected eye movement of the user is analyzed by the CPU 111 of the device 110. In this step, the eye movement pattern included in the detected eye movement and time period for completing the eye movement pattern is specified by the CPU 111 of the device 110. The CPU 111 determines the eye movement pattern by comparing detected eye movement with the eye movement patterns stored in the storage 113. If the eye movement pattern is specified, then the CPU 111 specifies the time period for completing the specified eye movement pattern by calculating total eye gaze time for the specified eye movement pattern. In this step, the position of the specified eye movement pattern on the display 114 may also be specified by the CPU 111.

At step S106, a command associated with a combination of the eye movement pattern and the threshold time period for the eye movement pattern is determined by the CPU 111. In this step, the CPU 111 searches the storage 113 to find the eye movement pattern to which the specified eye movement pattern matches. Then the CPU 111 determines whether the specified time period for completing the specified eye movement pattern fulfills the predetermined threshold time period associated with the matched eye movement pattern. If the specified time period fulfills the predetermined threshold time period, a command, associated with combination of the matched eye movement pattern and the predetermined threshold time period for the matched eye movement pattern, is determined by the CPU 111.

In step S106, if positions of eye movement pattern on the display are also associated with the combinations of eye movement pattern and threshold time period and the position of the specified eye movement pattern on the display 114 is specified by the CPU 111, a command, associated with combination of three elements including the matched eye movement pattern, threshold time period for the matched eye movement pattern and position of the matched eye movement pattern on the display, is determined by the CPU 111.

At step S108, the CPU 111 executes the determined command and then the computer device 110 is operated in accordance with the command.

These and other features and advantages of the present principles may be readily ascertained by one of ordinary skill in the pertinent art based on the teachings herein. It is to be understood that the teachings of the present principles may be implemented in various forms of hardware, software, firmware, special purpose processors, or combinations thereof.

Most preferably, the teachings of the present principles are implemented as a combination of hardware and software. Moreover, the software may be implemented as an application program tangibly embodied on a program storage unit. The application program may be uploaded to, and executed by, a machine comprising any suitable architecture. Preferably, the machine is implemented on a computer platform having hardware such as one or more central processing units ("CPU"), a random access memory ("RAM"), and input/output ("I/O") interfaces. The computer platform may also include an operating system and microinstruction code. The various processes and functions described herein may be either part of the microinstruction code or part of the application program, or any combination thereof, which may be executed by a CPU. In addition, various other peripheral units may be connected to the computer platform such as an additional data storage unit.

It is to be further understood that, because some of the constituent system components and methods depicted in the accompanying drawings are preferably implemented in software, the actual connections between the system components or the process function blocks may differ depending upon the manner in which the present principles are programmed. Given the teachings herein, one of ordinary skill in the pertinent art will be able to contemplate these and similar implementations or configurations of the present principles.

Although the illustrative embodiments have been described herein with reference to the accompanying drawings, it is to be understood that the present principles is not limited to those precise embodiments, and that various changes and modifications may be effected therein by one of ordinary skill in the pertinent art without departing from the scope or spirit of the present principles. All such changes and modifications are intended to be included within the scope of the present principles as set forth in the appended claims.

The invention claimed is:

1. A computer device operable with a user's eye movement, the device comprising:
   a detector for detecting the user's eye movement;
   a processor configured to:
   analyze the user's eye movement to specify an eye movement pattern in the detected user's eye movement from one eye gaze position to another eye gaze position and a time period for completing the eye movement pattern;
   determine a command associated with a combination of the eye movement pattern and the time period, wherein the command is determined based on the combination of the eye movement pattern from the one eye gaze position to the another eye gaze position and the time period for completing the eye movement pattern from the one eye gaze position to the another eye gaze position, wherein the command is generated if the time period for completing the eye movement pattern is less than a threshold time period, and different threshold time periods can be associated with the same eye movement pattern to generate different commands; and
   operate the device according to the command.

2. The device according to claim 1, wherein the detector is configured to collect the user's eye gaze positions,
   wherein the processor is further configured to:
   determine if the collected user's eye gaze positions conform with another eye movement pattern.

3. The device according to claim 1, wherein the device further comprises a display, wherein the processor is configured to identify a left, middle or right position of the detected eye movement pattern on the display and wherein the command is further determined based on the identified left middle or right position of the detected eye movement pattern on the display.

4. The computing device of claim 1, wherein the computing device is an eBook-reader.

5. A method for operating a computer device with user's eye movement, comprising:
   detecting the user's eye movement;
   analyzing the user's eye movement from one eye gaze position to another eye gaze position to specify an eye movement pattern in the detected user's eye movement and a time period for completing the eye movement pattern;
   determining a command associated with a combination of the eye movement pattern and the time period, wherein the command is determined based on the combination of the eye movement pattern from the one eye gaze position to the another eye gaze position and the time period for completing the eye movement pattern from the one eye gaze position to the another eye gaze position, wherein the command is generated if the time period for completing the eye movement pattern is less than a threshold time period, and different threshold time periods can be associated with the same eye movement pattern to generate different commands; and
   operating the device according to the command.

6. The method according to claim 5, wherein the detecting includes collecting the user's eye gaze positions;
   wherein the analyzing includes:
   determining if the collected user's eye gaze positions conform with another eye movement pattern.

7. The method according to claim 5, wherein the device comprising a display, wherein the analyzing further identifies a left, middle, or right position of the detected eye movement pattern on the display and wherein the command is further determined based on the identified left, middle or right position of the detected eye movement pattern on the display.

8. The method of claim 5, wherein the computing device is an eBook-reader.

\* \* \* \* \*